(12) United States Patent
Sexton

(10) Patent No.: US 8,978,189 B1
(45) Date of Patent: Mar. 17, 2015

(54) OMNIBRUSH

(71) Applicant: Curtis Bernard Sexton, Phoenix, AZ (US)

(72) Inventor: Curtis Bernard Sexton, Phoenix, AZ (US)

(*) Notice: Subject to any disclaimer, the term of this patent is extended or adjusted under 35 U.S.C. 154(b) by 0 days.

(21) Appl. No.: 14/328,828

(22) Filed: Jul. 11, 2014

(51) Int. Cl.
A61C 17/22 (2006.01)
A46B 13/02 (2006.01)
A46B 9/04 (2006.01)
A46B 15/00 (2006.01)

(52) U.S. Cl.
CPC ............. *A46B 9/045* (2013.01); *A46B 15/0036* (2013.01); *A46B 15/0034* (2013.01); *A46B 2200/1066* (2013.01)
USPC ................................ 15/28; 15/22.1; 15/167.2

(58) Field of Classification Search
CPC .... A61C 17/22; A61C 17/222; A61C 17/228; A61C 17/24; A61C 17/26; A46B 9/045; A46B 13/02; A46B 13/008
USPC ............ 15/22.1, 23, 28, 167.2; 601/139, 141, 601/142
See application file for complete search history.

(56) References Cited

U.S. PATENT DOCUMENTS

| 2,206,726 | A | * | 7/1940 | Lasater ........................... 15/188 |
| 4,224,710 | A |   | 9/1980 | Solow |
| 5,170,525 | A | * | 12/1992 | Cafaro .............................. 15/28 |
| 5,177,827 | A | * | 1/1993 | Ellison ........................... 15/22.1 |
| 5,337,435 | A | * | 8/1994 | Krasner et al. .................... 15/23 |
| 7,168,122 | B1 | * | 1/2007 | Riddell ........................... 15/22.1 |
| 8,584,291 | B2 |   | 11/2013 | Thompson |
| 8,631,531 | B2 | * | 1/2014 | Garner et al. ................... 15/22.1 |
| 2005/0172429 | A1 | * | 8/2005 | Russell et al. ................. 15/22.1 |
| 2011/0072605 | A1 |   | 3/2011 | Steur |
| 2013/0014331 | A1 |   | 1/2013 | Garner et al. |
| 2013/0067665 | A1 |   | 3/2013 | Sowinski |

FOREIGN PATENT DOCUMENTS

| GB | 2475489 | * | 6/2013 |
| WO | 2009/048287 | * | 4/2009 |

* cited by examiner

*Primary Examiner* — Mark Spisich
(74) *Attorney, Agent, or Firm* — Luca D'Ottone; KB Patents

(57) ABSTRACT

The inventive device object of the present application is an innovative automatic toothbrush that fits like a mouth guard between the user's top and bottom teeth. Moving bristles will clean all around each tooth at the same time, so teeth can be cleaned well and in less time than using a conventional toothbrush. Omnibrush is a revolutionary new way to have enhanced dental care. It fits around the top and bottom teeth like a mouth guard. There are bristles for the outside, the inside and the tops and bottoms of each individual tooth. While positioned comfortably within the mouth, the bristles will work automatically to clean every tooth thoroughly. The unit is electrically powered, using a charger or rechargeable batteries. The cleaning bristles can be replaced when they become worn, eliminating the need to replace the whole cleaning unit. It will be available in a small size so children can use it as well.

7 Claims, 7 Drawing Sheets

OMNIBRUSH

BACKGROUND OF THE INVENTION

1. Field of the Invention

The inventive device disclosed in the present application generally relates to dental cleaning products and more specifically to an innovative automatic toothbrush that fits like a mouth guard between the user's top and bottom teeth.

2. Brief Description of the Prior Art

Whole mouth toothbrush are well known in the art. For example, U.S. Pat. No. 8,584,291 to Thompson discloses and claims, a whole mouth toothbrush with an elongate hollow handle portion, and attached U shaped brush retaining portion. The housing holds an electric motor, a battery power supply, a microprocessor, a printed circuit board and an on-off switch. Under the teachings of the Thompson patent a primary drive belt connects the motor shaft to a first brush spindle. A plurality of secondary drive belts connect the first brush spindle to the remaining brush spindles. Each spindle terminates in a rotating brush head. Upper brush heads brush the user's top teeth and the lower spindles brush the user's bottom teeth. The microprocessor is programmed to cause the brush retaining shafts to cycle back and forth from a clockwise rotation to a counter clockwise rotation.

In addition to that, U.S. Pat. No. 4,224,710 to Solow discloses and claims, a power-actuated toothbrush is provided and in its broadest aspects, the toothbrush brushes both sides of a tooth and penetrates into the embrasures. The bristles of the Solow device extend at an angle to the sides of the teeth whereby the bristles of the brush also enter and clean the sulcus area. In preferred embodiments of the invention, the biting surfaces of the teeth are cleaned simultaneously with the sides of the teeth. In other embodiments of the invention, an entire dental arch or even the entire mouth of teeth is cleaned in a single operation.

U.S. Published Patent Application No. 20130067665 to Sowinski also discloses a hands-free simultaneous whole-mouth teeth cleaner is disclosed for brushing a user's teeth all at once, without requiring manual manipulation, thereby enabling the user to engage in other activities while his teeth are being brushed. The hands-free simultaneous whole-mouth teeth cleaner disclosed by Sowinski includes top and bottom brush trays which include tooth-brushing material (such as bristles) for contacting the user's teeth, a motor housed within a motor case located in the space formed by the brush trays, and a switch for actuating the motor. In some embodiments the hands-free simultaneous whole-mouth teeth cleaner includes a handle for easy insertion and removal. In some embodiments, the tooth-brushing material is capable of contacting all sides of a user's teeth, as well as the gum line. Other embodiments include an external surface capable of providing non-irritating frictional contact to soft tissue of a user's mouth.

U.S. Published Patent Application No. 20130014331 to Garner discloses, a full mouth toothbrush for simultaneously brushing the facial, lingual, occlusal and incisal surfaces of all the maxillary and mandibular teeth is provided. Under the teachings of Garner's patent, the full mouth toothbrush can include a handle, a power source, a motor assembly, and a drive assembly. The full mouth toothbrush can further include a mouthpiece configured to collectively contact multiple surfaces of multiple teeth simultaneously that brushes and, thus, cleans the teeth and gums.

Finally, U.S. Patent Application No. 20110072605 to Steur discloses, a mouthpiece that includes a mouthpiece body having portions configured to receive the user's upper and lower sets of teeth when it is inserted into the user's mouth. Mounted in the receiving portions are teeth-cleaning assemblies, which include bristles for cleaning of the teeth and a system for moving the bristles against the teeth to scrub and clean the teeth. Control elements for the cleaning assemblies are actuated by a selected interior portion or element of the user's mouth, such as the tongue, cheek, lips or jaw.

Despite all the efforts listed above prior art patents describe structures that are either not truly convenient or else involve complicated, expensive, and overly difficult assembly and/or disassembly parts and procedures. Other devices have been advertised on various media but never patented or described into a printed publication.

SUMMARY OF THE INVENTION

The invention is an innovative automatic toothbrush that fits like a mouth guard between the user's top and bottom teeth. Moving bristles will clean all around each tooth at the same time, so teeth can be cleaned well and in less time than using a conventional toothbrush.

It is then the principal object of the present invention is to a quick and easy way to clean one's teeth thoroughly, and it can also be used to clean dentures as well. It is a secondary objective of the present invention to provide a device that is electrically powered so a thorough cleaning job is done automatically, and it is rechargeable.

It is an additional objective of the present invention to provide a device that does not rusts or deteriorate over time and that can be safely installed over a television set. It is a final objective of the present invention to provide for a device that is relatively inexpensive to built and set up, but can eventually be sold at a premium.

These and other objective achieved by the device of the present invention will be apparent by the drawings, by their detailed description, and by the specification here from appended.

DESCRIPTION OF THE PREFERRED EMBODIMENT

Figure 1:
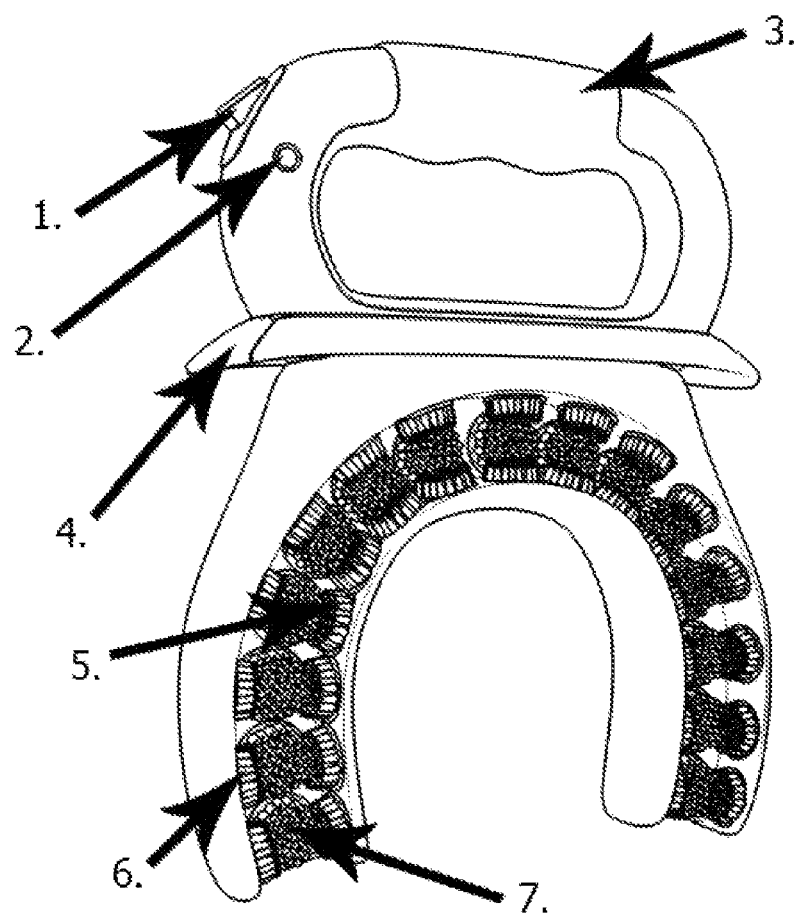
FIG. 1 is a perspective view of "Omnibrush" in accordance with the teaching of the present invention.
Figure 2:
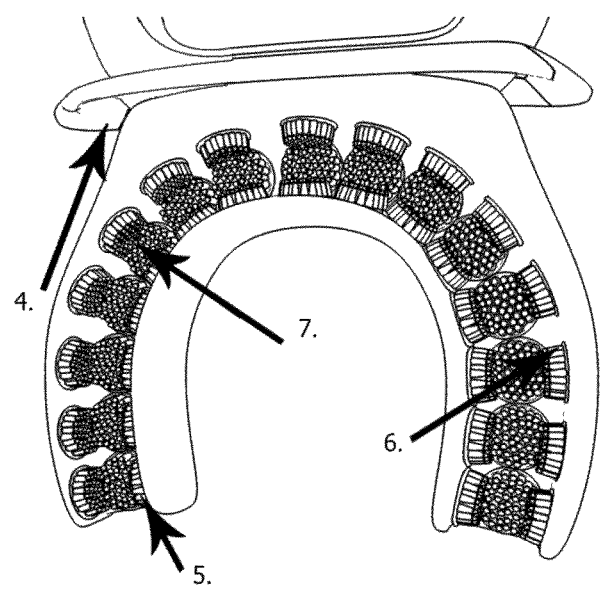
FIG. 2 is a top perspective view of "Omnibrush" of FIG. 1 and all its features.
Figure 3:
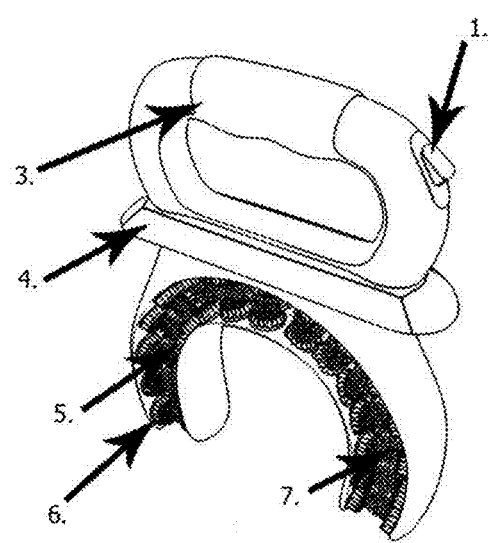
FIG. 3 is a perspective view of "Omnibrush" of FIG. 1.
Figure 4:
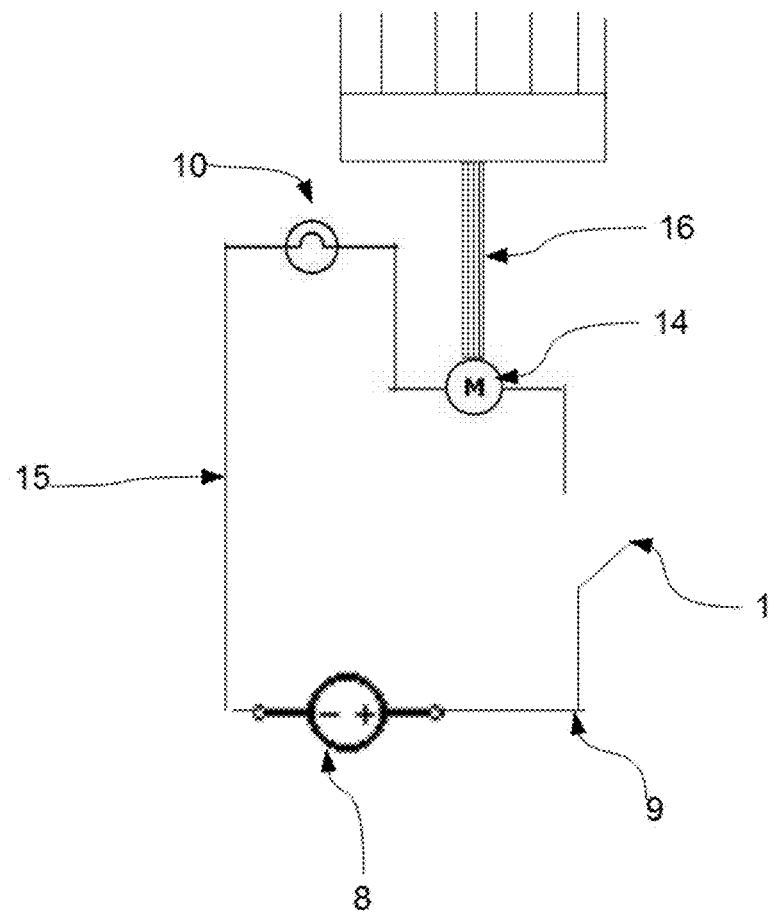
FIG. 4 is a diagrammtic view of the electrical components of one of the preferred embodiments of the "Omnibrush" of the present application.
Figure 5:
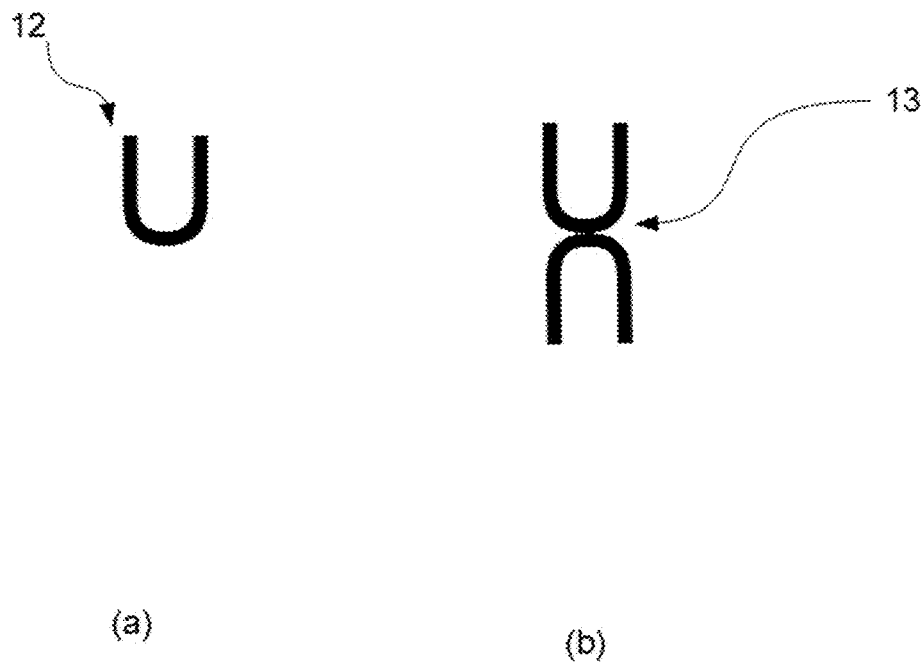
FIG. 5 is a cross section view of the mouth guard (4) of the present invention showing a simple U structure (12) it can only be used to clean one set of teeth at one time, in the case of the inverted U or double U (13) it can clean the teeth on both the upper and lower jaws at the same time.
Figure 6:
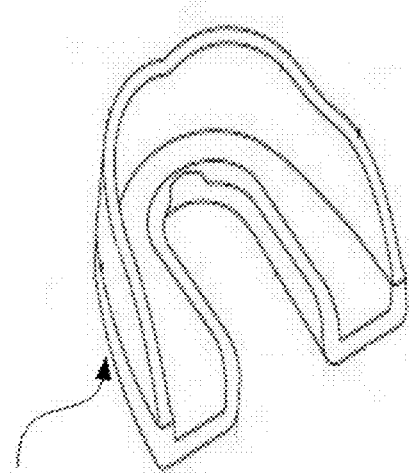
FIG. 6 shows a mouth guard.
Figure 7:
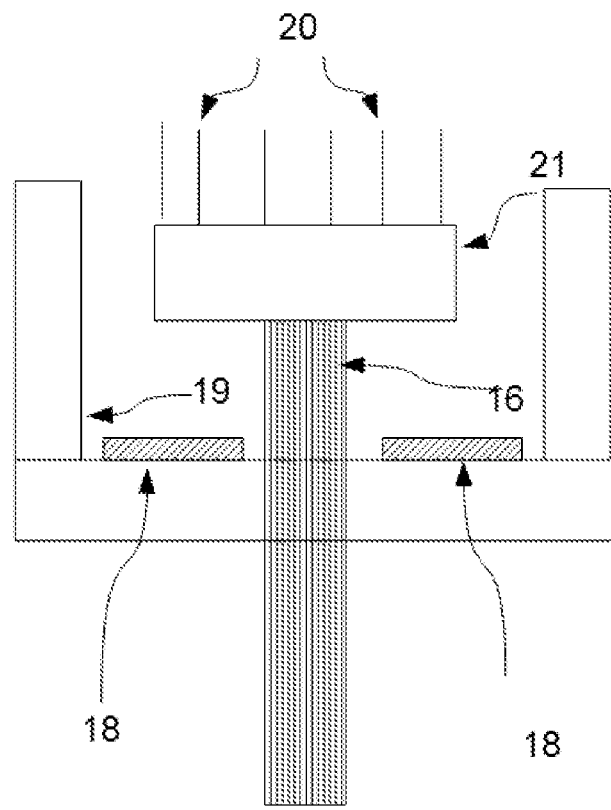
FIG. 7 is a cross sectiona view of the Omnibrush of the present application showing the structural relationship between the functional elements composing the device.

The invention is an innovative automatic toothbrush that fits like a mouth guard between the user's top and bottom teeth. Moving bristles will clean all around each tooth at the same time, so teeth can be cleaned well and in less time than using a conventional toothbrush. As it can be inferred from the drawings essential elements of the Omnibrush of the present application include: an ON switch (1) connected to a power source via a first electrical circuitry; powering a LED light (2), located on the handle (3) of the Omnibrush device. Where said handle (3) is attached to a mouth guard (4) featuring a semi circular base member having U or opposite U shaped cross section. Where said cross sections of said semi circular base member are covered with inner brushes (5), center brushes (7), and outer brushes (6).

For the purpose of the present application a LED is a light-emitting diode: a semiconductor light source. LEDs are used as indicator lamps in many devices and are increasingly used for other lighting. Appearing as practical electronic components in 1962, early LEDs emitted low-intensity red light, but modern versions are available across the visible, ultraviolet, and infrared wavelengths, with very high brightness.

In a separate preferred embodiment of the Omnibrush of the present application said plurality of brushes including said inner brushes (5), center brushes (7), and outer brushes (6) are circularly propelled to a rotating motion via an electrical circuitry activated by said ON switch (1) and powered by said power source.

In a separate preferred embodiment a UV source is place in the inside surface of said U shaped or opposite U shaped base member. To have them thing in between said plurality of brushes including said inner brushes (5), center brushes (7), and outer brushes (6), the UV light may be dispensed via fiber optics.

Omnibrush is a revolutionary new way to have enhanced dental care. It fits around the top and bottom teeth like a mouth guard. There are bristles for the outside, the inside and the tops and bottoms of each individual tooth. While positioned comfortably within the mouth, the bristles will work automatically to clean every tooth thoroughly. The unit is electrically powered, using a charger or rechargeable batteries. The cleaning bristles can be replaced when they become worn, eliminating the need to replace the whole cleaning unit. It will be available in a small size so children can use it as well.

In one of the preferred embodiments of the present invention the disclosed device is an automated toothbrush consisting of an ON switch (1) connected to a power source (8) via a first electrical circuitry (9) where said power source (8) powers a light (10) that may be a LED light (2) located on the handle (3) of the Omnibrush device, where said handle (3) is attached to a mouth guard (4) featuring a semi circular base member (11) covered with inner brushes (5), center brushes (7), and outer brushes (6).

Said mouth guard (4) comprises a semi circular base member having a U structure running around it or alternatively a double U or U and inverted U structure. In the cause of a simple U structure (12) it can only be used to clean one set of teeth at one time, in the case of the inverted U or double U (13) it can clean the teeth on both the upper and lower jaws at the same time.

The automated toothbrush of the present application may further comprise an electrical motor (14) electrically connected to said power source (8) via a second electrical circuitry (15). Said electrical motor is mechanically connected to said plurality of brushes (5-7) via a bearing system (16) imparting them a rotating motion.

In a separate preferred embodiment of the present application the automated toothbrush further comprising a UV source (18) that may be placed in between the inside surface (19) of said U shaped cross section and said plurality of brushes (5-7). Said UV source is a flat optic fiber electrically connected to said power source.

The power source may be a battery such as rechargeable or replaceable battery. An electrical connection may be departing from the automated toothbrush of the present application to recharge the power source.

An electric battery is a device consisting of one or more electrochemical cells that convert stored chemical energy into electrical energy. Each cell contains a positive terminal, or cathode, and a negative terminal, or anode. Electrolytes allow ions to move between the electrodes and terminals, which allows current to flow out of the battery to perform work.

Primary (single-use or "disposable") batteries are used once and discarded; the electrode materials are irreversibly changed during discharge. Common examples are the alkaline battery used for flashlights and a multitude of portable devices. Secondary (rechargeable batteries) can be discharged and recharged multiple times; the original composition of the electrodes can be restored by reverse current. Examples include the lead-acid batteries used in vehicles and lithium ion batteries used for portable electronics. Batteries come in many shapes and sizes, from miniature cells used to power hearing aids and wristwatches to battery banks the size of rooms that provide standby power for telephone exchanges and computer data centers.

Batteries have much lower specific energy (energy per unit mass) than common fuels such as gasoline. This is somewhat mitigated by the fact that batteries deliver their energy as electricity (which can be converted efficiently to mechanical work), whereas using fuels in engines entails a low efficiency of conversion to work.

An optical fiber (or optical fibre) is a flexible, transparent fiber made of extruded glass (silica) or plastic, slightly thicker than a human hair. It can function as a waveguide, or "light pipe", to transmit light between the two ends of the fiber. Power over Fiber (PoF) optic cables can also work to deliver an electric current for low-power electric devices. The field of applied science and engineering concerned with the design and application of optical fibers is known as fiber optics.

Optical fibers are widely used in fiber-optic communications, where they permit transmission over longer distances and at higher bandwidths (data rates) than wire cables. Fibers are used instead of metal wires because signals travel along them with less loss and are also immune to electromagnetic interference. Fibers are also used for illumination, and are wrapped in bundles so that they may be used to carry images, thus allowing viewing in confined spaces. Specially designed fibers are used for a variety of other applications, including sensors and fiber lasers.

Optical fibers typically include a transparent core surrounded by a transparent cladding material with a lower index of refraction. Light is kept in the core by total internal reflection. This causes the fiber to act as a waveguide. Fibers that support many propagation paths or transverse modes are called multi-mode fibers (MMF), while those that only support a single mode are called single-mode fibers (SMF). Multi-mode fibers generally have a wider core diameter, and are used for short-distance communication links and for applications where high power must be transmitted. Single-mode fibers are used for most communication links longer than 1,000 meters (3,300 ft).

Each of said brushes (5-7) generally comprises a plurality of bristles (20) mounted on a generally oblong base (21).

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An automated toothbrush comprising:
   a) a handle;
   b) a power source;
   c) a motor;
   d) an on/off switch provided on the handle which operatively engages the motor with the power source;
   e) a light source provided on the handle; and
   f) a mouth guard provided on the handle and including a semi-circular base member defining U-shaped channels in upper and lower portions thereof, said channels being adapted to receive the teeth of both the upper and lower jaws at the same time, each of the U-shaped channels including:
   i) a plurality of inner, center and outer brushes each including a substantially disk-shaped base having a plurality of bristles extending from a face thereof, each of the plurality of inner, center and outer brushes being serially arranged along the length of each of the U-shaped channels, each of the brushes being rotatably driven by the motor such their axes of rotation is substantially parallel to the respective bristles with the rotation axis of each of the center brushes being substantially perpendicular to that of the adjacent inner and outer brushes, the brush arrangement enabling the cleaning of the top, inner and outer sides of the teeth of both upper and lower jaws at the same time.

2. The automated toothbrush of claim 1 where said light is a LED.

3. The automated toothbrush of claim 1 further comprising a UV source.

4. The automated toothbrush of claim 3 where said UV source is placed in between the inside surface of said U shaped channels and said inner brushes.

5. The automated toothbrush of claim 3 where said UV source is placed in between the inside surface of said U shaped channels and said center brushes.

6. The automated toothbrush of claim 3 where said UV source is placed in between the inside surface of said U shaped channels and said outer brushes.

7. The automated toothbrush of claim 3 where said UV source is a flat optic fiber.

* * * * *